United States Patent [19]

Asano et al.

[11] Patent Number: 4,938,897
[45] Date of Patent: Jul. 3, 1990

[54] CHLORAMBUCIL DERIVATIVES AND CELL-DISCRIMINATING AGENT CONTAINING THE SAME

[75] Inventors: Kiro Asano; Humio Tamura, both of Inashiki; Tsuyoshi Saito, Toride; Hisayuki Wada, Matsudo; Yoichi Suzuki, Tokyo, all of Japan

[73] Assignee: Kureha Kagaku Kogyo Kabushiki Kaisha, Tokyo, Japan

[21] Appl. No.: 873,812

[22] Filed: Jun. 13, 1986

[30] Foreign Application Priority Data

Jun. 21, 1985 [JP] Japan .................. 60-135791

[51] Int. Cl.$^5$ .................. C07J 1/00; A61K 31/56
[52] U.S. Cl. .................. 514/169; 552/626; 552/625
[58] Field of Search .................. 514/169; 260/397.1

[56] References Cited

U.S. PATENT DOCUMENTS

| | | | |
|---|---|---|---|
| 3,963,707 | 6/1976 | Hogberg | 260/239.55 D |
| 4,029,778 | 6/1977 | Fex et al. | 424/243 |
| 4,150,126 | 4/1979 | Fex et al. | 424/238 |
| 4,177,269 | 12/1979 | Fex et al. | 424/243 |
| 4,180,504 | 12/1979 | Hansen et al. | 260/239.55 |
| 4,181,669 | 1/1980 | Hansen et al. | 260/397.4 |
| 4,261,910 | 4/1981 | Asano et al. | 260/397.5 |
| 4,332,797 | 6/1982 | Asano et al. | 424/238 |

FOREIGN PATENT DOCUMENTS

| | | |
|---|---|---|
| 1016959 | 1/1966 | United Kingdom . |
| 2028335 | 3/1980 | United Kingdom . |

OTHER PUBLICATIONS

Journal of Medicinal Chemistry, vol. 11, No. 5, p. 1106 (1968).
Journal of Medicinal Chemistry, vol. 12, pp. 810-818 (1969).
Journal of Medicinal Chemistry, vol. 15, No. 11, pp. 1158-1169 (1972).
K. Sempuku, "Estradiol-17α Derivatives", Chemical Abstracts, vol. 96, No. 11, p. 621, Abstract No. 85849p.

*Primary Examiner*—Nicholas S. Rizzo
*Attorney, Agent, or Firm*—John P. White

[57] ABSTRACT

Disclosed herein are (1) a fluorescent substance represented by the formula (I), (2) a process for producing the fluorescent substance, and (3) a cell-discriminating agent containing the fluorescent substance as an active ingredient.

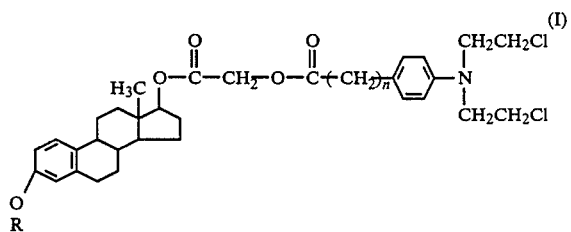

(wherein n is an integer of 0, 1, 2 or 3 and R represents a residual radical of a fluorescent material.)

6 Claims, 8 Drawing Sheets

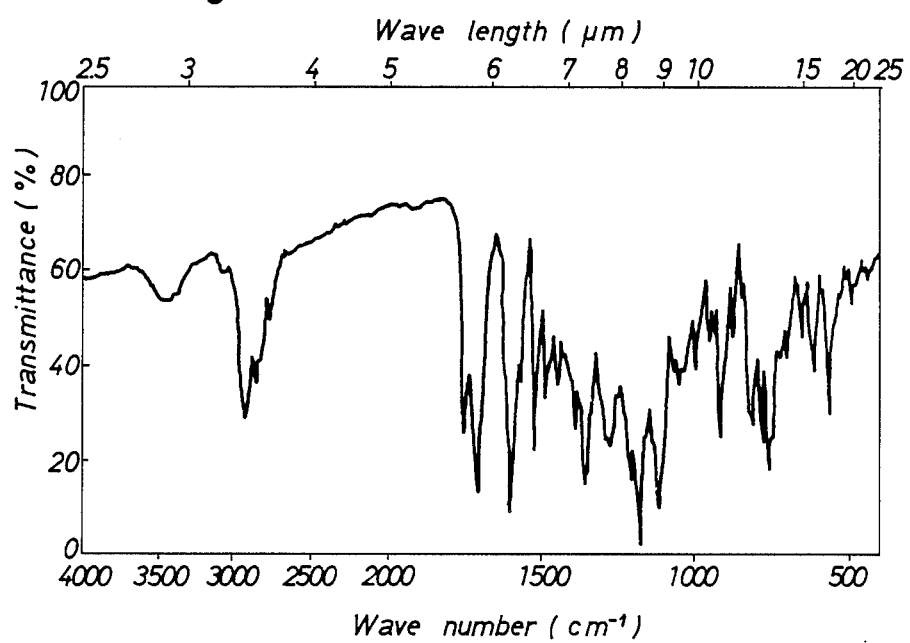

CHLORAMBUCIL DERIVATIVES AND CELL-DISCRIMINATING AGENT CONTAINING THE SAME

BACKGROUND OF THE INVENTION

The present invention relates to (1) a novel fluorescent substance produced by substituting a hydrogen atom of the hydroxy group on 3-position of estradiol moiety of a compound synthesized by conjugating estradiol and chlorambucil with a fluorescent material, (2) a process for producing the novel fluorescent substance and (3) a cell-discriminating agent containing the novel fluorescent substance.

Hitherto, trials of conjugating a human hormone and an anticancer medicine, administering the thus prepared compound to a cancer patient, thereby concentrating the anticancer medicine into the specified organ having the receptor of the hormone and attacking the cancer intensively have been carried out.

However, such trials have not exhibited any anticipated effectiveness due to the following reasons.

(1) The specificity of the hormone and/or the anticancer medicine is lost by the conjugation.

(2) Even in the case where the conjugating has been accomplished favorably, since the thus prepared substance attacks both normal and tumor cells, the reduction of the side effect of the antitumor medicine has not been effected to the expected extent.

(3) Because of the unstable bond between the hormone and the antitumor medicine, free antitumor medicine isolates from the conjugated substance and exerts its side effect to the patient.

Formerly, the present inventors have studied the conjugated compound of estradiol and chlorambucil, and have found an unexpected fact that the conjugated compound concentrates onto the tumor cells in a large amount as compared to the normal cells when the hydrogen atom of the hydroxy group on 3-position of estradiol moiety is substituted by an acyl group, more in detail, by acetyl group, propionyl group, butyryl group or benzoyl group, and based on their finding, the present inventors have developed an anticancer medicine having a high anticancer activity and a low side effect.

However, since the precise behavior of the conjugated compounds in a human body, which is necessary for knowing the reason why the conjugated compound concentrates onto the tumor cells at a high concentration, has not been elucidated, it was difficult to further develop the better conjugated compounds along with this idea utilizing the precious and unexpected finding.

Of course, there is a method for observing the behavior of the conjugated compound in a human body by utilizing the radio-labelled conjugated compound, however, the development has not been to the expected extent because of the following reasons;

(1) the radio-labelled, conjugated compound cannot be administered in a large amount to a human body, (2) it is not easy to prepare the labelled compound, and (3) determination of radioactivity necessitates an intricated apparatus and complicated procedures.

On this account, as a result of the present inventors' study, it is found that by joining a fluorescent material to the conjugated compound of estradiol and chlorambucil, which make the compound possible to be easily determined and observed by sight, difficult problems how to maintain the property of the conjugated compound to concentrate onto tumor cells in a large amount compared to normal cells have been solved, and based on the finding, the present inventors have attained the present invention.

SUMMARY OF THE INVENTION

In a first aspect of the present invention, provided there is a fluorescent substance represented by the formula (I):

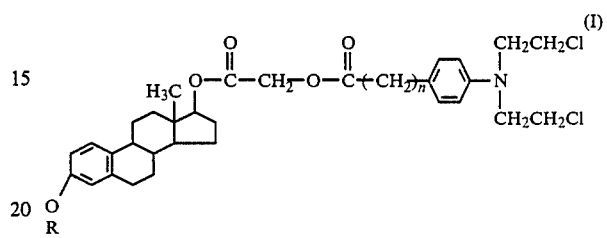

wherein n is an integer of 0, 1, 2 or 3 and R represents a residual radical of a fluorescent material.

In a second aspect of the present invention, provided there is a process for producing the fluorescent substance represented by the formula (I), comprising the steps of (1) reacting a fluorescent material with estradiol represented by the formula (II):

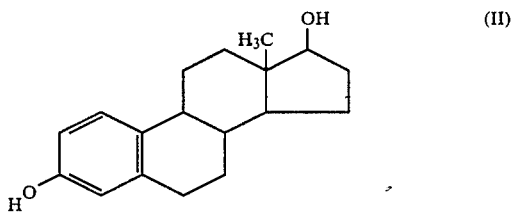

wherein the hydroxy group at 17 position is 17-α or 17-β and "estradiol" includes the salts thereof, thereby obtaining a derivative of estradiol represented by the formula (III):

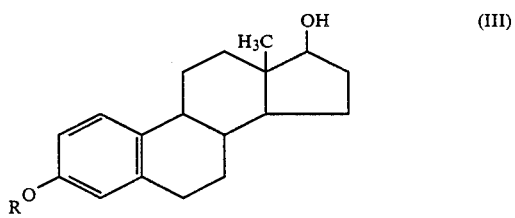

wherein R represents a residual radical of the fluorescent material, (2) reacting the thus obtained derivative of estradiol with a compound represented by the formula (IV):

$$X-CH_2COY \qquad (IV)$$

wherein X represents a halogen atom or a hydroxy group and Y represents a hydroxy group or a halogen atom, thereby obtaining a compound represented by the formula (V):

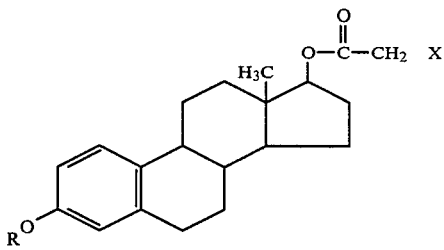

wherein X and R are respectively the same as defined above and (3) reacting the obtained compound represented by the formula (V) with an alkylating agent represented by the formula (VI), a chloride thereof or a salt thereof:

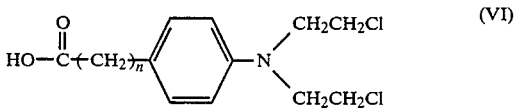

(wherein n is an integer of 0, 1, 2 or 3.) to obtain the compound represented by the formula (I):

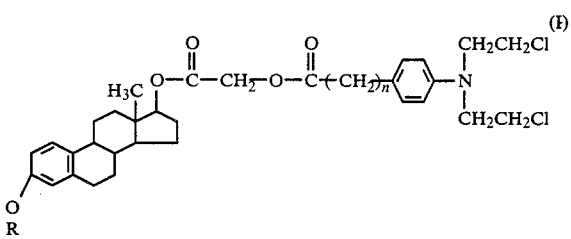

wherein n is an integer of 0, 1, 2 or 3 and R represents a residual radical of the fluorescent material.

In a third aspect of the present invention, provided there is a cell-discriminating agent containing the fluorescent substance represented by the formula (I).

The principal objective of the present invention lies in obtaining a fluorescent substance, the behavior of which in a living body can be visually recognized by a simple procedure. Another objective of the present invention lies in obtaining a cell-discriminating agent which concentrates selectively onto tumor cells and makes possible to recognize the tumor cells visually by the fluorescence emitted from the agent.

The fluorescent substance according to the present invention is a conjugated compound of estradiol and chlorambucil, and the hydrogen atom of the hydroxy group at 3-position of the estradiol moiety has been substituted by a fluorescent material.

BRIEF EXPLANATION OF DRAWINGS

FIG. 4 is an infrared absorption spectrum of 3-dansyloxyestradiol-17α-[[4-[p-{bis(2-chloroethyl)amino}phenyl]-butyryloxy]]acetate synthesized also in Example 1 and FIG. 5 is an infrared absorption spectrum of 3-dansyloxyestradiol-17β-[[1-[p-{bis(2-chloroethyl)amino}phenyl]carbonyloxy]]acetate synthesized in Example 3.

All the FIGS. 6–8 are shapes of cells observed by fluorescent microscope.

Figure 6A:
Figure 6B:
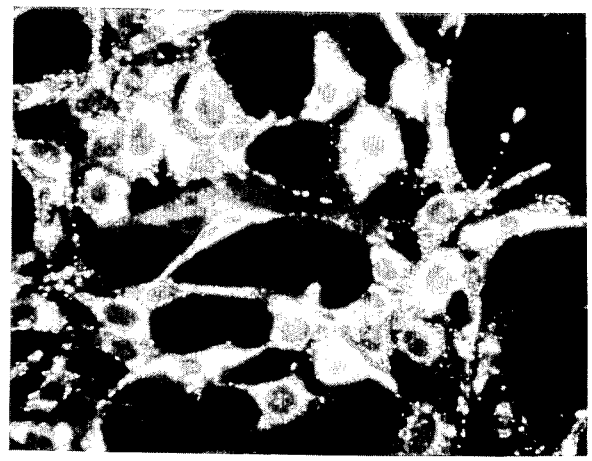
Figure 6C:
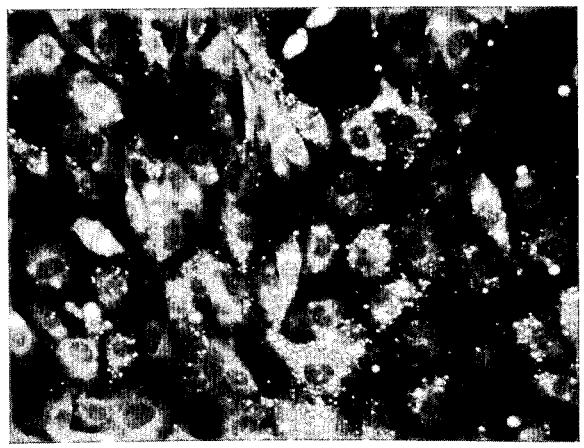
Figure 6D:
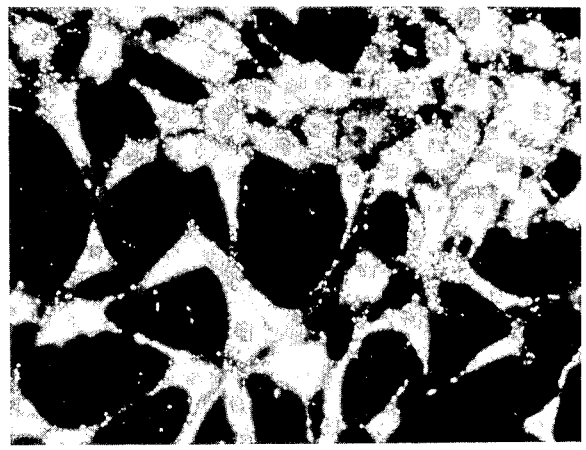

FIG. 6(A) shows the shape of 3T3 cells incubated in the culture medium of a concentration of the test substance of 10 μg/ml at a pH of 6.5 for 4 days, FIG. 6(B) is the shape of 3T3 SV-40 cells incubated under the same conditions, FIG. 6(C) shows the shape of 3T3 cells incubated in the culture medium of a concentration of the test substance of 50 μg/ml at a pH of 7.8 for 4 days and FIG. 6(D) shows the shape of 3T3 SV-40 cells incubated under the same conditions as 6(C), these incubations being carried out in Example 7.

Figure 7A:
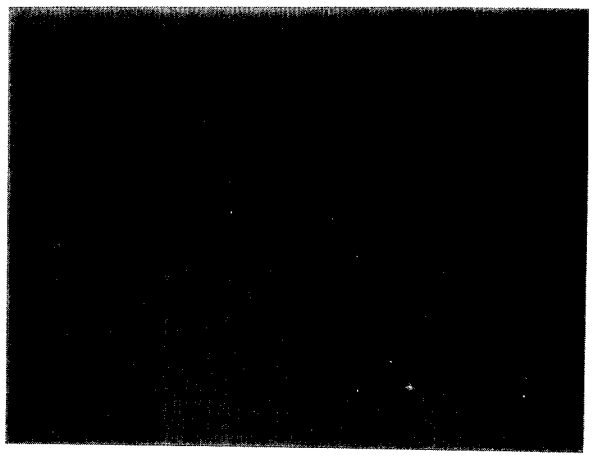
Figure 7B:
Figure 7C:
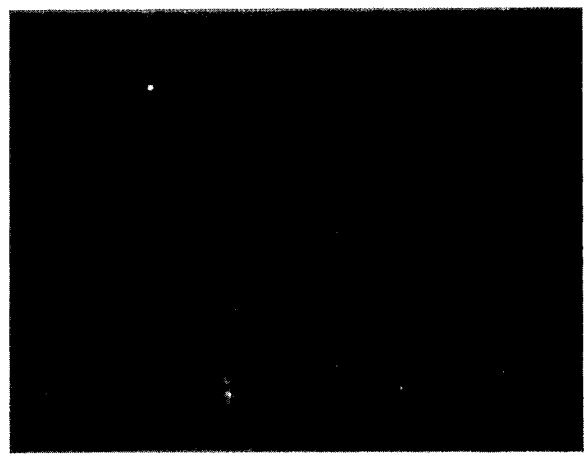
Figure 7D:
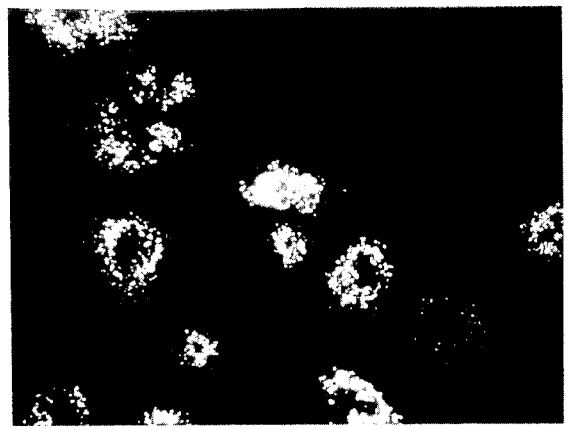

FIG. 7(A) shows the shape of the normal human renal cell (FLOW 4000) incubated for 11 days at 37° C. in the culture medium of the concentration of the test substance of 10 μg/ml at a pH of 7.8, FIG. 7(B) shows the shape of the human renal cancer cells (RC) incubated under the same conditions as 7(A), FIG. 7(C) shows the shape of the normal human renal cells (FLOW 4000) incubated under the same conditions as 8(A) except for the temperature of 40° C. and FIG. 7(D) shows the shape of the human renal cancer cells (RC) incubated under the same conditions as 7(C), these incubations having been carried out in Example 8.

Figure 8A:
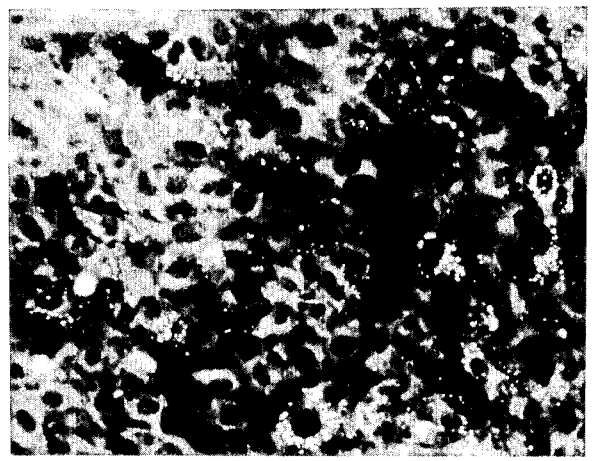
Figure 8B:

FIG. 8(A) shows the shape of 3T3 cells incubated in a culture medium containing the test substance at a concentration of 5 μg/ml at a pH of 6.5 for 4 days and FIG. 8(B) shows the shape of 3T3 SV-40 cells incubated under the same conditions as 8(A), these incubations having been carried out in Example 9.

DETAILED DESCRIPTION OF THE INVENTION

The fluorescent substance according to the present invention (hereinafter referred to as the present substance) is represented by the formula (I):

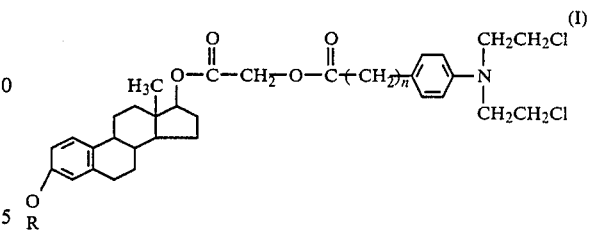

wherein n is an integer of 0, 1, 2 or 3 and R represents a residual radical of a fluorescent material.

The present substance is produced, for example, as follows.

As the first step, estradiol represented by the formula (II) or a salt thereof and a fluorescent material are reacted in an organic solvent at a temperature of from 0° to 50° C. for from one minute to 74 hours to obtain a derivative of estradiol represented by the formula (III):

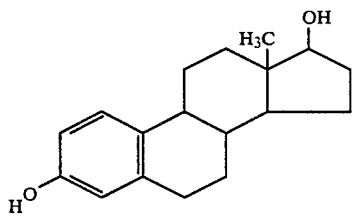
(II)

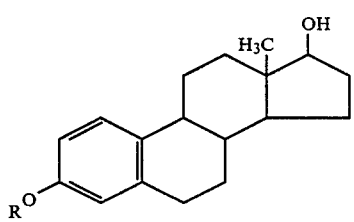
(III)

In the formula (II), the hydroxy group at 17-position of estradiol is 17-α or 17-β and in the formula (III), R represents a residual radical of the fluorescent material. Namely, in the derivative of estradiol represented by the formula (III), the estradiol moiety is joined to the moiety of the fluorescent material at 3-position.

Any fluorescent material can be used in the above-mentioned reaction, however, the following materials are exemplified:

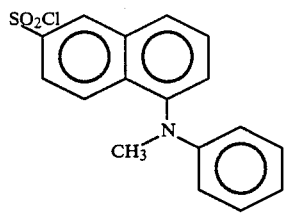

N-methyl-2-anilino-napthalene-6-sulfonyl chloride

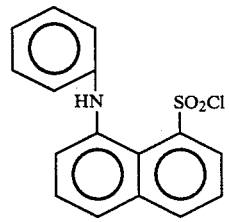

1-anilinonaphthalene-8-sulfonyl chloride

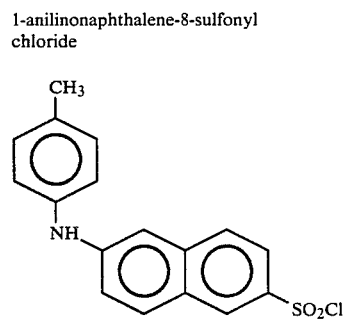

N-(p-tolyl)-2-amino-naphthalene-6-sulfonyl chloride

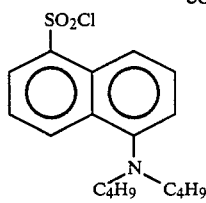

1-di-n-butylaminonaphthalene-5-sulfonyl chloride

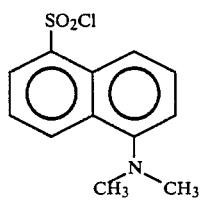

1-dimethylaminonaphthalene-5-sulfonyl chloride

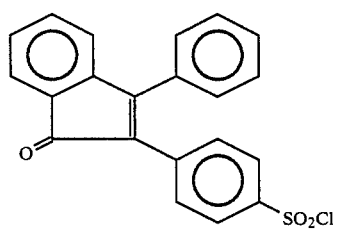

2-(p-chlorosulfophenyl)-3-phenyl indone

In the second step, the thus obtained derivative of estradiol represented by the formula (III) and a compound represented by the formula (IV), $$X-CH_2CO-Y \qquad (IV)$$

[wherein X represents a halogen atom or a hydroxy group and Y represents a hydroxy group or a halogen atom] are reacted in an organic solvent, for instance, anhydrous tetrahydrofuran, acetone, carbon tetrachloride or benzene at a temperature of from −20° to 100° C. for from 1 to 74 hours to obtain another derivative of estradiol represented by the formula (V):

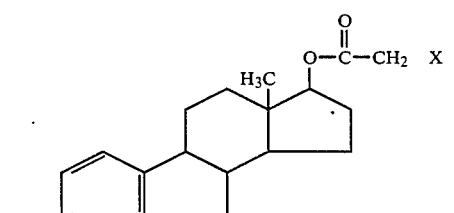
(V)

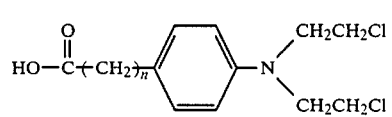
(VI)

[wherein X represents a hydroxy group or a halogen atom and in formula (VI), n is an integer of 0, 1, 2 or 3.]

In the third step, the thus obtained derivative of estradiol represented by the formula (V) and an alkylating agent represented by the formula (VI), a salt thereof or a chloride thereof are reacted in an organic solvent, for example, dimethylsulfoxide, dimethylformamide, pyridine, acetone, methanol, tetrahydrofuran, toluene, carbon tetrachloride or chloroform at a temperature of from −20° to 100° C., preferably from 0° to 60° C. for from 1 to 74 hours to obtain a reaction product, and it is purified by a conventional method to obtain the present compound represented by the formula (I).

In the above reaction of the third step, p-toluenesulfonic acid.hydrochloride may be added.

In addition, the order of the steps in the process for producing the present substance may be changed as the case demands, for example, as follows.

(i) An alkylating agent represented by the formula (VI), a salt thereof or a chloride thereof is brought into reaction with a compound represented by the formula (IV) in an organic solvent at a temperature of from −20° to 100° C. for from 1 to 74 hours, and after purifying the reaction product, the purified product is further reacted with a derivative of estradiol represented by the formula (III) in an organic solvent at a temperature of from 0° to 100° C. for from one minute to 74 hours to obtain the present substance represented by the formula (I).

(ii) Estradiol represented by the formula (II) and a compound represented by the formula (IV) are reacted in an organic solvent at a temperature of from −20° to 100° C. for from 1 to 74 hours, and after purifying the reaction product, the ester group at 3-position of the purified reaction product is subjected to hydrolysis to obtain a derivative of estradiol represented by the formula (VII):

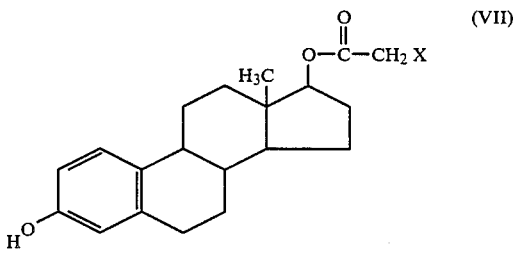

(X is a hydroxy group or a halogen atom)

Then, the thus obtained derivative of estradiol is reacted with an alkylating agent represented by the formula (VI), a salt thereof or a chloride thereof in an organic solvent at a temperature of from −20° to 100° C., preferably from 0° to 60° C. for from 1 to 74 hours to obtain a reaction product, and after purifying the reaction product, the purified compound represented by the formula (VIII) is reacted with a fluorescent material to produce the present substance represented by the formula (I).

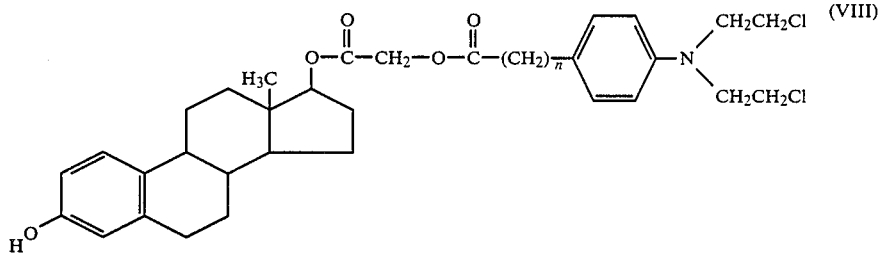

(n is an integer of 0, 1, 2 or 3)

In addition, in the last mentioned reaction, p-toluenesulfonic acid.hydrochloride may be added.

The above-mentioned process for producing the present substance will be easily understood by the non-limitative Examples which will be given later, and as the results of confirming the structure of the present substance thus obtained by means of infrared absorption spectrography, ultraviolet absorption spectrography, nuclear magnetic resonance spectrography, elementary analysis, measurement of melting point and chromatography, it has been confirmed that the thus obtained present substance is the substance represented by the formula (I).

The feature of the present substance lies in the point that the present substance suppresses the tumor cells and hardly exerts influences on the normal cells.

In addition, since the present substance is fluorescent, the movement thereof in a living body after administration can be easily confirmed by examining the fluorescence appearing in the living body.

Particularly, such a property of the present substance is convenient for knowing the take-up amount of the present substance into the target cells.

It has been confirmed by in vitro test that the present substance suppresses the tumor cells at a temperature from ordinary temperature to 43° C. and at a pH of from 7.8 to 5.5. The present substance mainly suppresses tumor cells.

The present substance may be used in several forms and shapes of pharmaceutical composition as the active ingredient, for example, tablets, granules, powder and capsules for oral administration. These pharmaceutical composition may contain binders, vehicles, fillers, lubricants, surfactants and disintegrators. The composition may take liquid forms for oral administration such as aqueous or oily suspension, solution, syrup and mixtures. The present substance may be administered as suppository, and in it, liphophilic or hydrophilic base-material, stabilizer, disintegrator and colouring agent may be included. The composition may take the form of injection, and solubilizer, nutrient material, stabilizer and surfactant may be included therein. In addition, alkali, acid or salts may be added to the pharmaceutical composition within the allowed limitation in order to maintain or raise the activity of the present substance. Furthermore, the present substance may be percutaneously administered.

The additives and the carriers for preparing the pharmaceutical composition containing the present substance as the active ingredient are exemplified as follows.

They are lactose, saccharose, sorbitol, mannitol, potatostarch, cornstarch, amylopectin, various starches, crystalline cellulose, derivatives of cellulose (for example, carboxymethyl cellulose and methylcellulose), gelatin, magnesium stearate, polyvinyl alcohol, sodium alginate, calcium stearate, polyethylene glycol, propylene glycol, waxes, gum arabic, talc, titanium dioxide, silicic acid, vegetable oils such as olive oil, peanut oil and sesame oil, paraffin oil, cacao butter, alcohols such as ethanol and benzyl alcohol, aqueous physiological saline solution, sterilized water, glycerol, vaseline, polysorbate, sodium chloride and potassium chloride.

The pharmaceutical composition may contain from 0.01 to 90% by weight, preferably from 0.05 to 60% by weight of the present substance in unit dose form for oral and parenteral administration.

The fact that the present substance is extremely safe is shown by the result of acute toxicity test as follows.

To each of a group of ICR-JCL mouse of 4 weeks in age kept in a transparent cage, a solution of the present substance in olive oil was intraperitoneally administered by using a syringe at a rate of 80 mg/kg body weight. After administration, the treated mice (8 animals per group) were observed for one week as compared to those administered with olive oil only. Any abnormal symptom was not observed on the treated mice. No case of death was observed in the group at all.

On the other hand, all members of the mice of the same strain administered with chlorambucil at a rate of 80 mg/kg died just after the administration. For reference, $LD_{50}$ of chlorambucil on mouse is 20 mg/kg body weight of a mouse.

The present substance is used as an anticancer medicine.

As the cancers to which the present substance is applied, cancers of digestive tract, mammary cancer, lung cancer, cancer of the skin, cancer of the uterus, ovarian cancer, urinary cancer, prostate cancer, sarcoma of the stomach, lymphoma, cancer of the blood and myeloma may be mentioned. Transformed cells due to virus may be mentioned as the disease to be treated by the present substance.

In addition, the present substance is used as the agent by which the movement thereof in a living body is simply observed by fluorescent thereof. Namely, the present substance is used as the cell-discriminating agent. For the above-mentioned purposes, the present substance is used at a rate of from 0.01 to 50 mg/kg body weight.

The present invention will be explained more in detail while referring to the non-limitative examples as follows:

EXAMPLES

EXAMPLE 1

Synthesis of 3-Dansyloxyestradiol-17β-[[4-[p-{bis(2-chloroethyl)amino}pheny]butyryloxy]]acetate 1-1 Synthesis of 3-dansyloxy-17β-estradiol Into a four necked flask of 10 liters in capacity, 40 g (0.147 mol) of 17β-estradiol and 6667 ml of acetone were introduced, and after adding 148.8 ml of aqueous 1N solution of sodium hydroxide thereto, the mixture was brought into solution by stirring thereof. Then, a solution of 42 g (0.150 mol) of dansyl chloride (5-(dimethylamino)-1-naphthalenesulfonyl chloride) in 167 ml of acetone was added dropwise at 20° C. for 30 minutes into the solution, and the mixture was reacted at 40° C. for 90 minutes. After confirming by thin-layer chromatography (referred to as TLC) that a larger part of the mixture had reacted, the sodium chloride formed was removed by filtration of the reaction mixture, and after distilling off a larger part of acetone from the reaction mixture, the residue was cooled to 5° C. to precipitate the crystals. After collecting the crystals by filtration and washing the thus collected crystals with 20 ml of aqueous solution of acetone (acetone 90%), the washed crystals were recrystallized from 1050 ml of the aqueous 90% solution of acetone to obtain 47 g of the product melting at 182°–184° C.

Separately, the filtrate was condensed to obtain 24 g of a wet crystals, and by recrystallizing the wet crystals from 300 ml of the aqueous 90% acetone solution, 10 g of the product were recovered. Namely, the total amount of the product was 57 g in a yield of 75.2%.

TLC of the product while using the TLC solvent of the following composition gave three spots, Rf being 0.36:

Composition of the TLC solvent:

| chloroform | 18 ⎫ | | |
|---|---|---|---|
| | | 40 ⎫ | |
| ethanol | 1 ⎭ | | ⎬ |
| cyclohexane | | 60 ⎭ | |

The product was subjected to purification by column-chromatography as follows.

Figure 1:
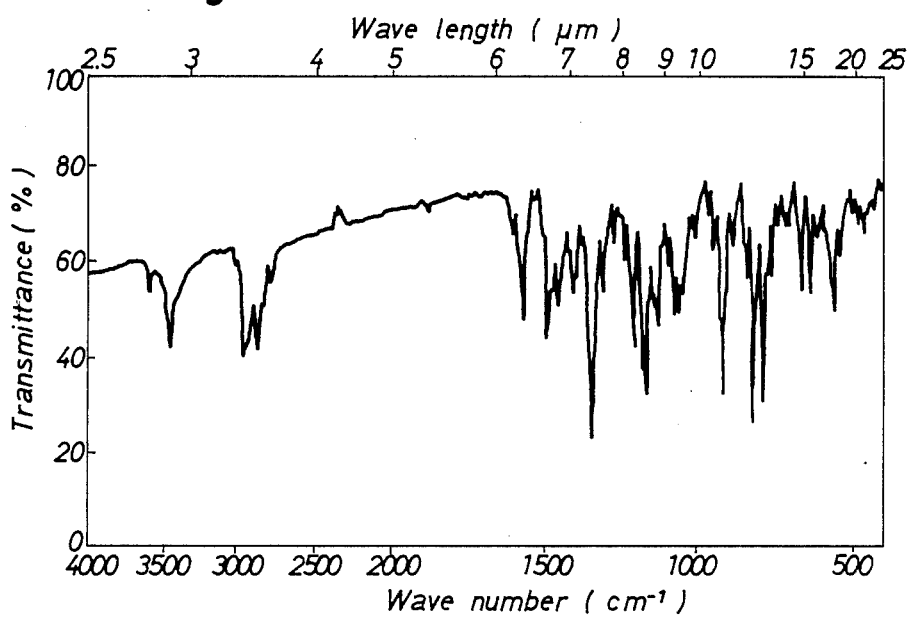
FIG. 1 is an infrared absorption spectrum of 3-dansyloxyestradiol-17β synthesized in Example 1.

Into a column prepared by filling 1.7 kg of silica gel in a glass tube of 75 mm in inner diameter and 1050 mm in length by using a 5:1 mixed solvent of chloroform and acetone, a solution of 57 g of the product dissolved in 200 ml of the 5:1 mixed solvent of chloroform and acetone by heating was charged, and the thus absorbed material on the column was fractionally eluted by the same mixed solvent at a flow rate of 11.1 ml/min (0.25 cm of the column/min). After discarding the fractions No. 1 to No. 10 as the impurifies, the fractions No. 11 to No. 25 which gave one spot on chromatography were recovered, and by condensing the thus recovered fractions (in total, 1500 ml), 50 g of pale yellow crystals melting at 184.5° C. were obtained. The thus purified crystal was 3-dansyloxy-17β-estradiol and its infrared absorption spectrum is shown in FIG. 1.

The outline of the above reaction scheme is as follows:

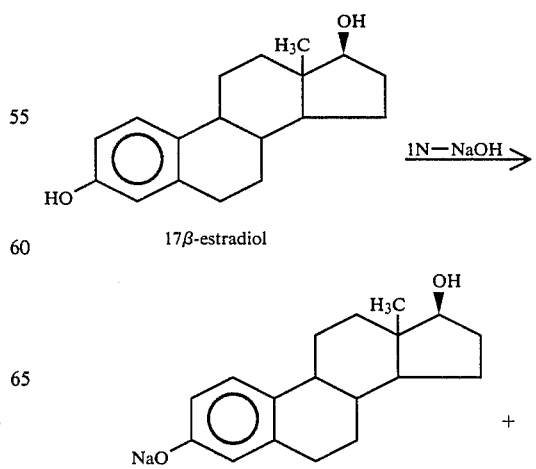

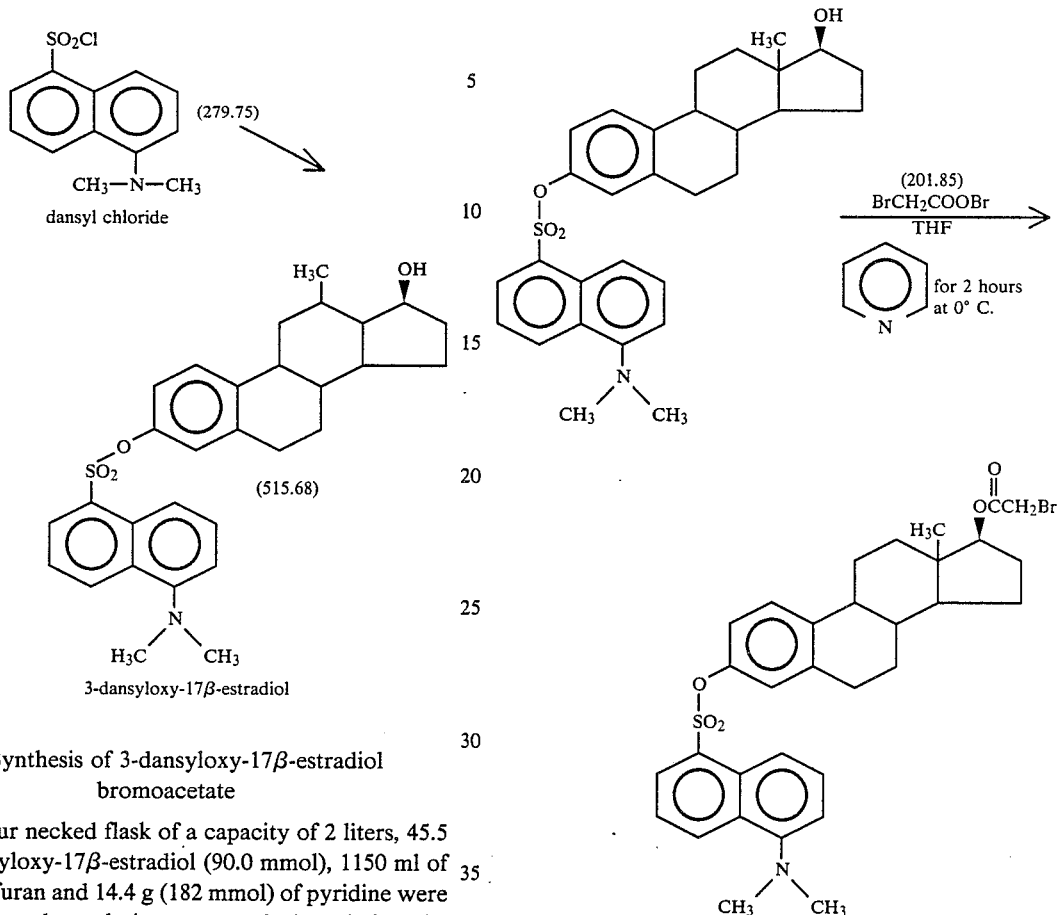

3-dansyloxy-17β-estradiol

1-2 Synthesis of 3-dansyloxy-17β-estradiol bromoacetate

Into a four necked flask of a capacity of 2 liters, 45.5 g of 3-dansyloxy-17β-estradiol (90.0 mmol), 1150 ml of tetrahydrofuran and 14.4 g (182 mmol) of pyridine were introduced, and a solution was made by stirring the content of the flask. After cooling the solution to 0°–1° C. with iced water, a solution of 36.4 g (180.3 mmol) of bromoacetyl bromide in 100 ml of tetrahydrofuran was added dropwise into the above solution within 40 minutes. The reaction mixture was subjected to maturation by leaving thereof at 0°–1° C. for 2 hours, at 5° C. for the next 2 hours and then at 15° C. for 2 hours, and the reaction mixture was left for a night at room temperature. After removing the formed pyridine hydrobromide by filtration and washing the precipitate with tetrahydrofuran, the filtrate and the washing were combined and subjected to distillation at a bath temperature of 30° C. under a reduced pressure to obtain 84 g of yellow crystals as the residue.

After dissolving the yellow crystals in 500 ml of dichloromethane at room temperature and washing the thus formed solution with cold water, the pH of the washed solution was made to 7 by stirring thereof with 500 ml of an aqueous 5% solution of sodium chloride and next with an aqueous solution of sodium hydrogencarbonate. After washing the thus treated solution with the aqueous 5% solution of sodium chloride (500 ml), the solution was dried on 20 g of anhydrous magnesium sulfate and dichloromethane was distilled off from the solution at a bath temperature of 30° C. under a reduced pressure to obtain 64 g of the crude product. The outline of the above reaction scheme is as follows:

The crude product obtained was purified as follows.

Into a column prepared by filling 1.3 kg of silica gel in a glass tube of 75 mm in inner diameter and 800 mm in length by using chloroform, a solution of 64 g of the crude product dissolved in 200 ml of chloroform was charged, and the adsorbed material on the silica gel was eluted fractionally by chloroform at a flow rate of about 50 ml/min to obtain fractions No. 1 to No. 25, which gave one spot on chromatography, in a total amount of 5 liters (200 ml of each fraction). The solid matter obtained by condensing 5 liters of the combined fractions was dissolved in 50 ml of chloroform, and the crystals obtained by adding 150 ml of hexane to the chloroform solution was washed with 50 ml of hexane and then dried to obtain 39 g of a fluorescent pale yellow crystalline substance melting at 147°–149° C. and giving one spot of thin layer chromatography (hereinafter referred to as TLC) (Rf of 0.37), the composition of the mixed solvent used in TLC being as follows:

| ethylacetate | 18 |     |
|---|---|---|
| ethanol | 1 | 20 |
| cyclohexane |  | 80 |

Figure 2:
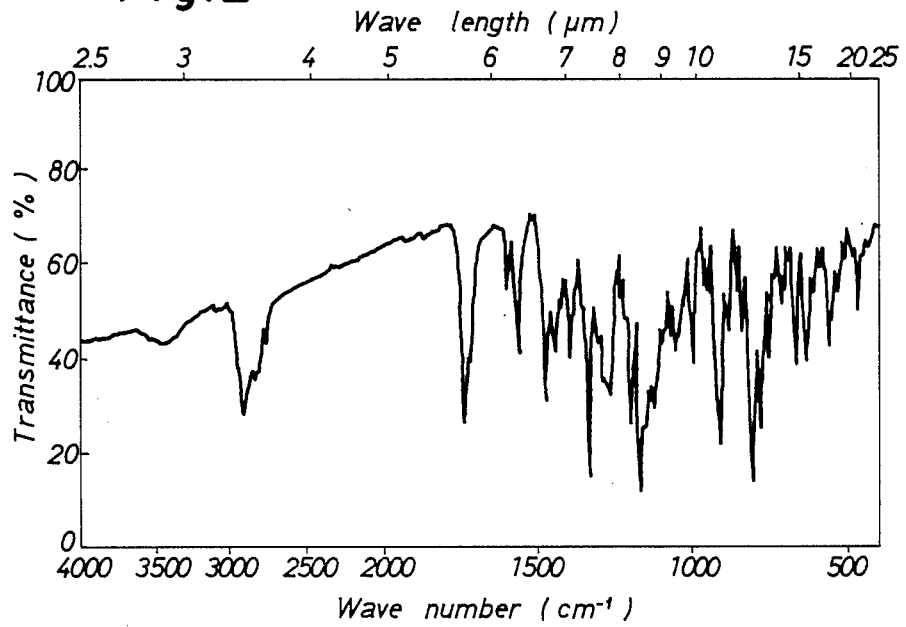
FIG. 2 is an infrared absorption spectrum of 3-dansyloxyestradiol-17β-bromoacetate synthesized in Example 1.

An infrared absorption spectrum of 3-dansyloxy-17β-estradiol bromoacetate is shown in FIG. 2.

1-3 Synthesis of 3-dansyloxyestradiol-17β-[[4-[p-{bis(2-chloroethyl)amino}phenyl]butyryloxy]]acetate At first, potassium N,N-di(2-chloroethyl)-γ-p-aminophenyl butyrate was produced by (1) dissolving 500 mg (1.644 mmol) of N,N-di(2-chloroethyl)-γ-p-aminophenylbutyric acid in 10 ml of methanol, (2)adding an aqueous solution, which was prepared by dissolving 107.2 mg of 86% potassium hydroxide in 4 ml of water, into the solution prepared in (1) and (3) drying the formed mixture under a reduced pressure by heating thereof on a water bath.

After adding 20 ml of tetrahydrofuran onto the prepared potassium N,N-bis(2-chloroethyl)-γ-p-aminophenylbutyrate, 626.6 mg (1.644 mmol) of 3-dansyloxyestradiol-17β-bromoacetate were added to the prepared mixture, and the whole mixture was reacted for 6 hours at 40° C. under stirring, and the reaction mixture was further stirred at room temperature while shielding from light for 16 hours.

Then, the solvent was distilled off from the reaction mixture under a reduced pressure, and the residue was purified by column chromatography with silica gel (made by Merck Co., under the registered trade name of KIESELGEL 40, No. 10180) while using a mixed solvent of a composition of cyclohexane/ethyl acetate/ethanol in the volume ratio of 83/16.1/0.9 as the developing solvent.

The Rf value of the obtained, purified residue on TLC (using a silica gel thin layer plate made by Merck Co. under the mark of LK6D) was 0.4 in the case where the above mixed solvent was used.

The melting point of the purified residue (which was amorphous) was 60° to 65° C., and the elementary analytical data thereof were as follows:

|  | C (%) | H (%) | N (%) | Cl (%) |
|---|---|---|---|---|
| Found | 64.7 | 6.8 | 3.2 | 8.2 |
| Calculated | 65.01 | 6.40 | 3.29 | 8.34 |

Figure 3:
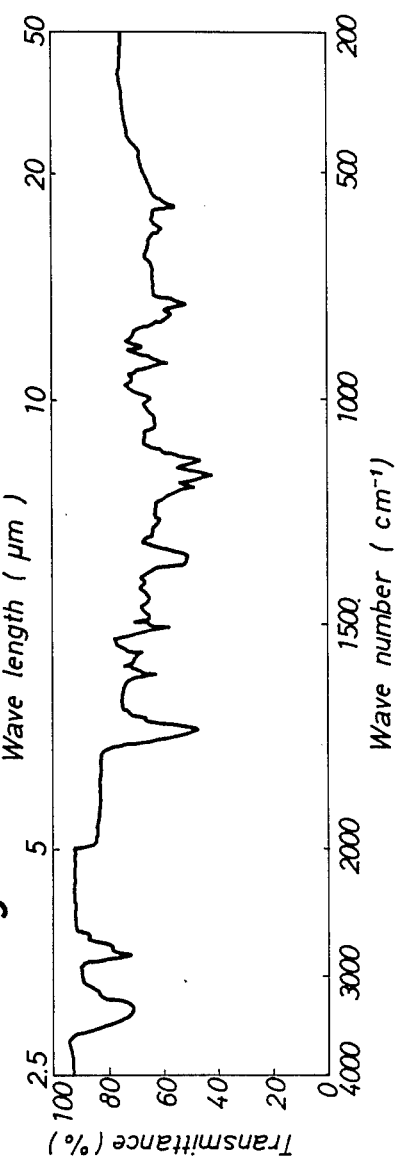
FIG. 3 is an infrared absorption spectrum of 3-dansyloxyestradiol-17β-[[4-[p-{bis(2-chloroethyl)amino}phenyl]-butyryloxy]]acetate synthesized in Example 1.

From the above analytical results and the infrared absorption spectrum shown in FIG. 3, it was found that the purified residue was the object substance, namely, 3-dansyloxyestradiol-17β-[[4-[p-{bis(2-chloroethyl)amino}phenyl]butyryloxy]]acetate.

As a result of fluorescent determination at a wave length of excitation light of 356 nm, the emitted light of 520 nm in wave length with ethyl acetate was observed.

Outline of the scheme of the above reactions is as follows:

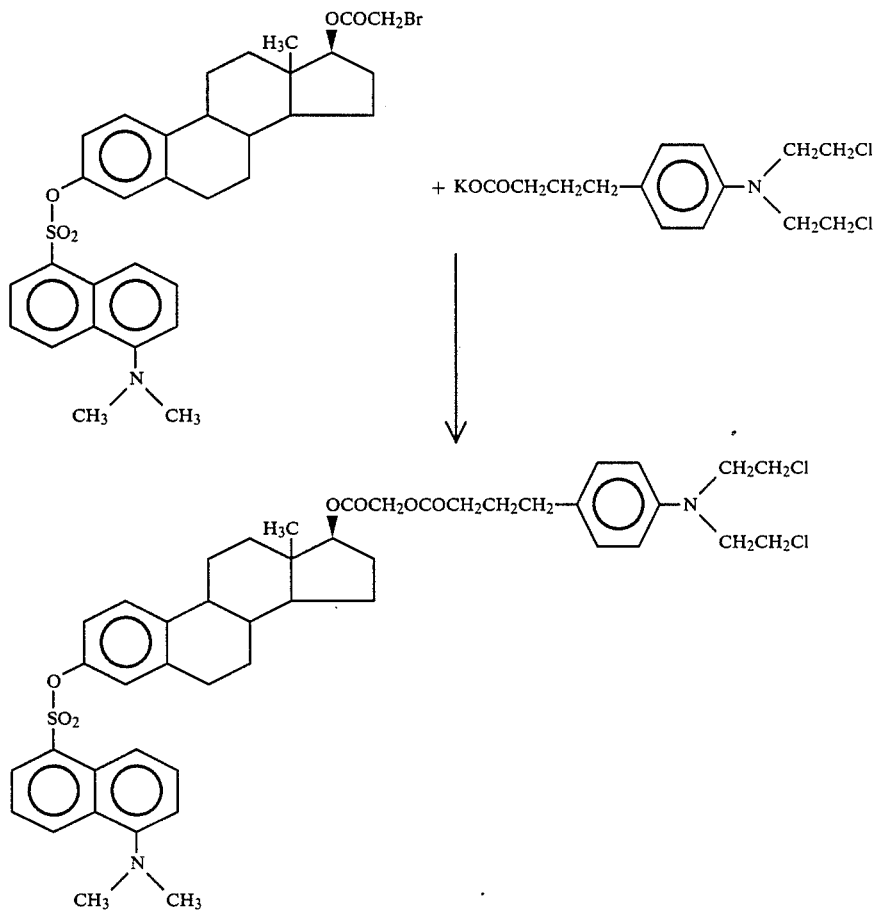

Figure 4:
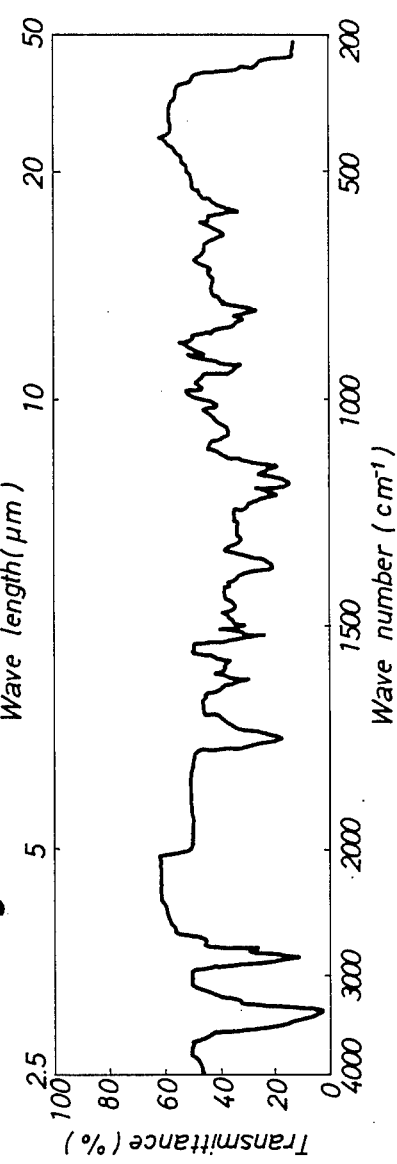

In addition, in the same manner as in (1-1), (1-2) and (1-3) of this Example, 3-dansyloxyestradiol-17α-[[4-[p-{bis(2-chloroethyl)amino}phenyl]butyryloxy]]acetate was synthesized, and its infrared absorption spectrum is shown in FIG. 4.

As a result of fluorescent determination at a wave length of excitation light of 357 nm, the emitted light of 525 nm in wave length of this substance with ethyl acetate was observed.

EXAMPLE 2

Synthesis of 3-dansyloxyestradiol-17β-[[4-[p-{bis(2-chloroethyl)amino}phenyl]butyryloxy]]acetate In Example 2, the same end product as in Example 1 was synthesized through the different route as follows:

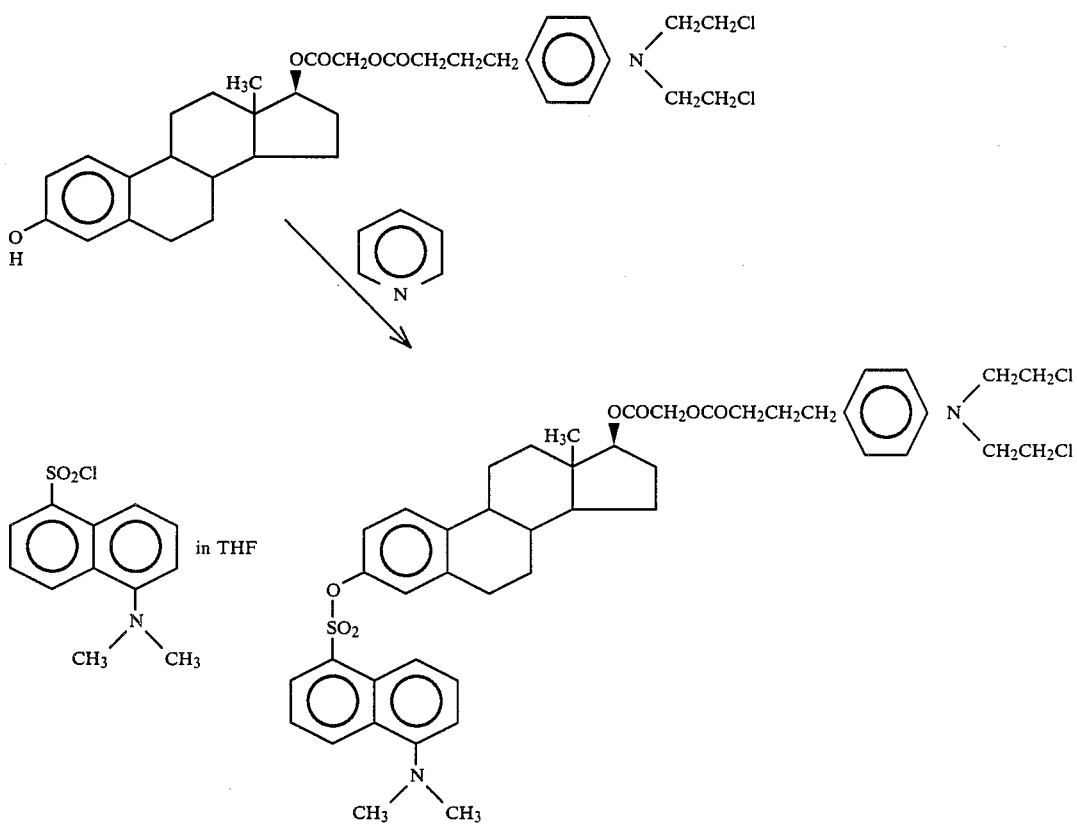

Namely, in 3 ml of benzene, 300 mg (0.487 mmol) of estra-1,3,5(10)-triene-3,17β-diol-17β-[[4-[p-{N,N-di-(2-chloroethyl)amino}phenyl]butyryloxy]]acetate were dissolved, and 1442 mg (0.535 mmol) of dansyl chloride and 42.2 mg (0.534 mmol) of pyridine were added to the formed solution, and the mixture was stirred for 60 minutes at room temperature. Then, the mixture was reacted for 5 minutes at 60° C. and further for 16 hours at room temperature while shielding from light. After ending the reaction, 5 ml of an aqueous 0.2N solution of hydrochloric acid were added to the reaction product, and pyridine hydrochloride was extracted by using a bortex mixer. After removing the aqueous layer, the benzene layer was washed twice with distilled water, and after subjecting the benzene layer to centrifuge, 5 ml of an aqueous 0.5N solution of sodium hydroxide were added to the layer. After shaking the mixture by the bortex mixer, the mixture was subjected to centrifuge and only the benzene layer was isolated and washed twice with each 5 ml of distilled water. After repeating the above operation of washing twice, the benzene layer was condensed under a reduced pressure. On subjecting the condensed material to thin layer chromatography with silica gel (the same gel as in Example 1) while using the same mixed solvent as in Example 1 as the developing solvent, the main spot was found at Rf of 0.4.

Then, the condensed material was purified by chromatography as in Example 1 to obtain the purified product which was confirmed as 3-dansyloxyestradiol-17β-[[4-[p-{bis(2-chloroethyl)amino}phenyl]butyryloxy]]acetate by the results of elementary analysis and infrared absorption spectrometry, etc.

EXAMPLE 3

Synthesis of 3-dansyloxyestradiol-17β-[[1-[p-{bis(2-chloroethyl)amino}phenyl]carbonyloxy]]acetate Into a round bottomed flask of 500 ml in capacity, 4.02 g (15.3 mmol) of 4-{bis(2-chloroethyl)amino}benzoic acid and 100 ml of methanol were introduced, and a solution was prepared by stirring the introduced substances. After further introducing an aqueous solution of 1.016 g (15.4 mmol) of 85% pottasium hydroxide in 20 ml of water into the flask, and stirring the mixture a while, methanol was distilled off from the mixture under a reduced pressure, and the residue was dehydrated in a freezing drier for 2 days.

After adding 100 ml of dimethyl sulfoxide to the dried residue and stirring the formed mixture to form a solution, 8.01 g (12.8 mmol) of 3-dansyloxyestradiol-17β-bromoacetate were added to the formed solution and the mixture was reacted for one hour at 40° C. and further for 16 hours at 30° C. under stirring. After removing dimethylsulfoxide from the reaction mixture under a reduced pressure of 2 mmHg at a bath temperature of 55° C., the residue was dissolved in 400 ml of chloroform, and the solution was washed twice with each 100 ml of water. After drying the washed solution on 8 g of anhydrous magnesium sulfate, chloroform was distilled off from the dried solution under a reduced pressure at a bath temperature of 30° to 35° C. to obtain 12 g of the crude product.

Onto a chromatographic column prepared by filling 400 g of silica gel (made by Merck Co. under the name of Art 7734) into a glass tube of 36 mm in inner diameter and 865 mm in length by using chloroform, a solution of 12 g of the crude product dissolved in 50 ml of chloroform was charged, and the absorbed product was subjected to elution by a flow of chloroform at a flow rate of 7 ml/min, thereby 1400 ml of a fraction showing one spot on the chromatogram were obtained. By condensing the fraction, 9 g of wet product were obtained. The wet product was dissolved in 30 ml of chloroform, and after adding 50 ml of hexane to the prepared solution, the mixture was cooled while stirring thereof, however, since no crystal was precipitated therefrom, the solvent was distilled off therefrom by using an evaporator and the residue was dried under vacuum to obtain 7 g of a solid, fluorescent substance in a yield of 68.2%. As a result of infrared absorption spectroscopy and elementary analysis, it was found that the solid material was the object substance. Its emission fluorescence was 521 nm by the excitation light of 358 nm. An infrared absorption spectrum of the substance is shown in FIG. 5.

In addition, the spot of the substance on TLC was Rf of 0.16 with the mixed solvent of chloroform and hexane of the ratio of 20:80 by volume.

Outline of the scheme of the above reactions is as follow:

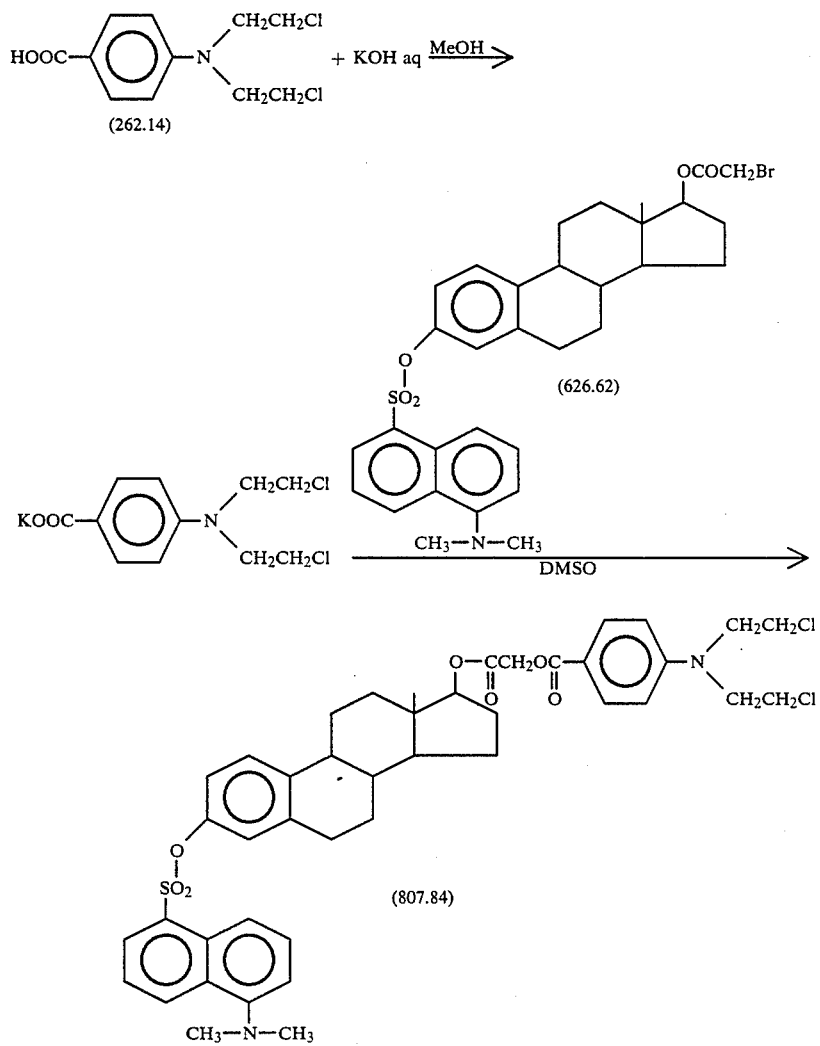

In the same manner as above, the following two substances were synthesized:

3-Dansyloxyestradiol-17β-[[2-[p-{bis(2-chloroethyl)amino}phenyl]acetoxy]]acetate, and 3-Dansyloxyestradiol-17β-[[3-[p-{bis(2-chloroethyl)amino}phenyl]propionyloxy]]acetate.

EXAMPLE 4

The activity of one of the present substances, 3-dansyloxyestradiol-17β-[[4-[p-{bis(2-chloroethyl)amino}phenyl]butyryloxy]]acetate in suppressing the proliferation of (1) the fibroblasts of mouse (3T3) and (2) transformed fibroblasts of mouse by SV-40 virus (3T3 SV-40) was studied by in vitro tests as follows:

Into a culture medium consisting of 90% by weight of DALBECCO MEM and 10% of bovine foetus serum, a solution of the test substance in dimethylsulfoxide at a rate of 5 μg/ml was added (dimethylsulfoxide being 1% of the culture medium). After adjusting the pH of the three culture media respectively to 6.5, 7.0 and 7.8, the target cells were implanted into each culture medium at a rate of $2 \times 10^4$ cells/ml, and the culture media were incubated at 37° C. in an atmosphere of 5% of carbon dioxide for 3 and 6 days. After ending the incubation, the number of living cells which were not dyed with Trypan blue enumerated in the cultured medium to calculate the rate of suppression of the proliferation of the fibroblasts as follows:

$$\text{Rate of suppression} = \frac{N_c - N_t}{N_c} \times 100$$

where $N_c$ is the number of the living fibroblasts in control group and $N_t$ is the number of living fibroblasts in the test group both in the unit area.

The test results are shown in Table 1.

TABLE 1

| | Rate of suppression (%) | | | |
|---|---|---|---|---|
| | 3T3 cells | | 3T3 SV-40 cells | |
| Days of culture | 3 | 6 | 3 | 6 |
| pH of | | | | |
| 6.5 | 16.8 | 14.76 | 64.19 | 91.60 |
| 7.0 | 6.45 | 20.03 | 55.80 | 85.88 |
| 7.8 | 7.87 | 11.30 | 31.60 | 38.80 |

As are seen in the table, the tested substance clearly showed an activity of suppressing the proliferation of transformed cells by SV-40 virus in a pH range of from 6.5 to 7.8.

In addition, a similar results was obtained in the test where 3-dansyloxyestradiol-17α-[[4-[p-{bis(2-chloroethyl)amino}phenyl]butyryloxy]]acetate was used.

EXAMPLE 5

The activity of one of the present substance, 3-dansyloxyestradiol-17β-[[4-[p-{bis(2-chloroethyl)amino}phenyl]butyryloxy]]acetate, in suppressing the proliferation of (1) human nomal renal cells (FLOW 4000) and (2) human renal cancer cells (RC) was examined as follows:

Into the same culture medium as in Example 4, a solution of the test substance dissolved in dimethylsulfoxide was added at a rate of 5 μg/ml (dimethylsulfoxide being 1% of the culture medium), and after adjusting the three culture media respectively to pH of 6.5, 7.0 and 7.8, the cells were implanted into each culture medium at a rate of $2 \times 10^4$ cells/ml, and the culture media implanted were incubated for 6 days at 37° C. in an atmosphere of 5% of carbon dioxide. The rate of suppression of the proliferation of the implanted cells was calculated by the same formula as in Example 4, the results being shown in Table 2.

TABLE 2

| | Rate of suppression (%) | |
|---|---|---|
| | FLOW 4000 cell | RC cell |
| pH of | | |
| 6.5 | 27.83 | 54.54 |
| 7.0 | 14.00 | 46.68 |
| 7.8 | −1.10 | 22.39 |

As are seen in the above table, the test substance according to the present invention clearly suppressed the proliferation of the human renal cancer cells (RC).

In addition, a similar result was obtained on another substance of the present invention, 3-dansyloxyestradiol-17α-[[4-[p-{bis-(2-chloroethyl)amino}phenyl]butyryloxy]]acetate.

EXAMPLE 6

The activity of one of the present substance, 3-dansyloxyestradiol-17β-[[2-[p-{bis(2-chloroethyl)amino}phenyl]acetoxy]]acetate in suppressing the proliferation of mouse fibroblasts (3T3) and SV-40 virus-transformed fibroblasts (3T3 SV-40) was examined by the same method as in Example 4 except for (1) the days of incubation of 3 and 5 days instead of 3 and 6 days in Example 4 and (2) the pH of the culture medium of 6.7 instead of 6.7, 7.0 and 7.8 in Example 4. The results are shown in Table 3.

TABLE 3

| Rate of suppression (%) | | | |
|---|---|---|---|
| 3T3 cells | | 3T3 SV-40 cells | |
| 3 days | 5 day | 3 days | 5 days |
| 25.24 | 53.28 | 55.72 | 85.86 |

In addition, as a result of the same test carried on another substance according to the present invention, 3-dansyloxyestradiol-17α-[[2-[p-{bis(2-chloroethyl)amino}phenyl]acetoxy]]acetate, the similar data were obtained.

EXAMPLE 7

Intaking of one of the present substances, 3-dansyloxyestradiol-17β-[[4-[p-{bis(2-chloroethyl)amino}phenyl]butyryloxy]]acetate, by mouse fibroblasts (3T3) and mouse transformed fibroblasts by SV-40 virus (3T3 SV-40) was examined with a fluorescence microscope under the following conditions:

Concentration of the test substance: 10 and 50 μg/ml
pH of culture medium: 6.5 and 7.8
Number of implanted cells: $2 \times 10^4$ cells/ml
Temperature and days of incubation: 37° C. for 5 days
Fixation: by aqueous 2.5% glutaraldehyde phosphate buffer for 90 minutes
Examination: by using a microscope (made by Olympus, BHS-RFK) with an exciting filter UGI and auxiliary absorption filter Y-475.

The intaking of the test substance by 3T3 SV-40 cells was remarkably recognized as compared to that by 3T3 cells. Refer to FIG. 6.

In addition, similar results were obtained concerning another substance of the present invention, 3-dansyloxyestradiol-17α-[[4-[p-{bis(2-chloroethyl)amino}phenyl]butyryloxy]]acetate.

EXAMPLE 8

In the similar manner to that in Example 7, intaking of one of the present substances, 3-dansyloxyestradiol-17β-[[4-[p-{bis(2-chloroethyl)amino}phenyl]butyryloxy]]acetate by the normal human renal cells (FLOW 4000) and the human renal cancer cells (RC) was examined by using the same fluorescence microscope as in Example 7. The incubation of the implanted cells was carried out at 37° and 40° C.

Intaking of the test substance by RC cells was remarkable as compared to that by the normal human cells (FLOW 4000) at both 37° and 40° C. of the incubation temperature. Refer to FIG. 7.

In addition, the same tendency was observed in the case where another substance of the present invention, 3-dansyloxyestradiol-17α-[[4-[p-{bis(2-chloroethyl)amino}phenyl]butyryloxy]]acetate was subjected to the same test.

EXAMPLE 9

In the similar manner to that in Example 6, intaking of one of the present substances, 3-dansyloxyestradiol-17β-[[2-[p-{bis(2-chloroethyl)amino}phenyl]acetoxy]]acetate by mouse fibroblast (3T3) and mouse transformed fibroblast by SV-40 virus (3T3 SV-40) was studied.

Intaking of the test substance by 3T3 SV-40 was remarkable as compared to that by 3T3. Refer to FIG. 8.

In addition, the similar result was observed in the case of 3-dansyloxyestradiol-17α-[[2-[p-{bis(2-chloroethyl)amino}phenyl]acetoxy]]acetate.

Examples of pharmaceutical composition of the present substance

One part of 3-dansyloxyestradiol-17β-[[4-[p-{bis(2-chloroethyl)amino}phenyl]butyryloxy]]acetate was added to 99 parts of dimethylsulfoxide and made solution by stirring. The solution was sterilized and prepared for injection.

What is claimed is:

1. A substance represented by the formula (I):

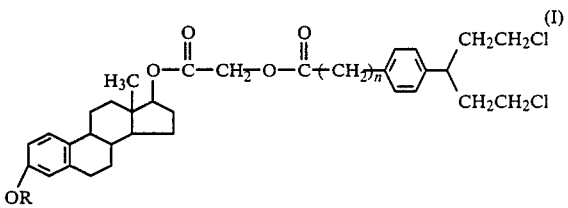

wherein n is an integer of 0, 1, 2, or 3 and R represents a dimethylaminonaphthalenesulfonyl group.

2. The substance according to claim 1, wherein the estradiol moiety of said substance is estradiol 17-α.
3. The substance according to claim 1, wherein the estradiol moiety of said substance is estradiol 17-β.
4. A tumor- or virus transformed-cell-discriminating agent comprising a substance represented by the formula (I):

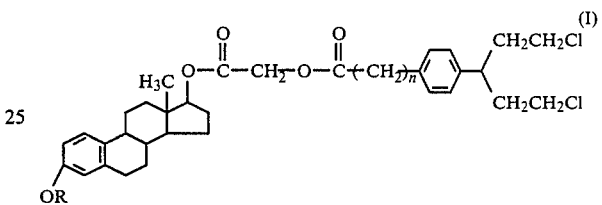

wherein n is an integer of 0, 1, 2, or 3 and R represents a dimethylaminonaphthalenesulfonyl group and a pharmaceutically acceptable carrier.

5. The tumor- or virus transformed-cell-discriminating agent according to claim 4, wherein the estradiol moiety of said substance is estradiol 17-α.
6. The tumor- or virus transformed-cell-discriminating agent according to claim 4, wherein the estradiol moiety of said substance is estradiol 17-β.

* * * * *

UNITED STATES PATENT AND TRADEMARK OFFICE
CERTIFICATE OF CORRECTION

PATENT NO. : 4,938,897
DATED : July 3, 1990
INVENTOR(S) : Kiro Asano et al.

It is certified that error appears in the above-indentified patent and that said Letters Patent is hereby corrected as shown below:

Columns 15 and 16, the structure which reads:

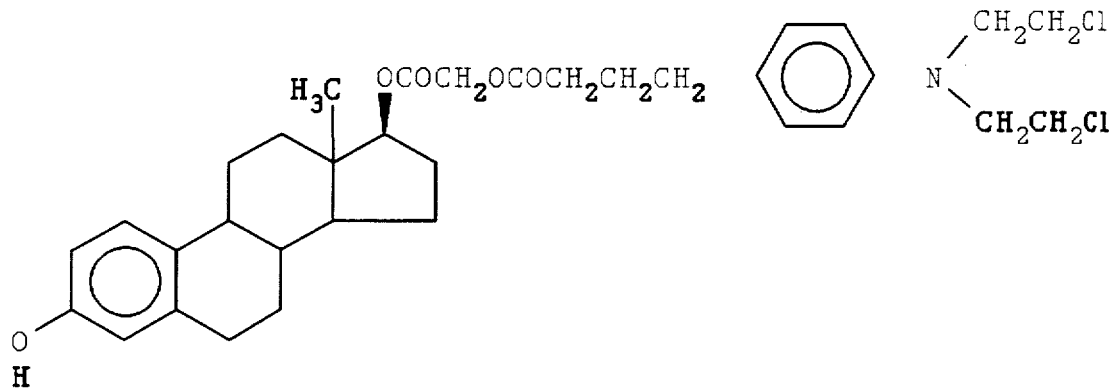

should read:

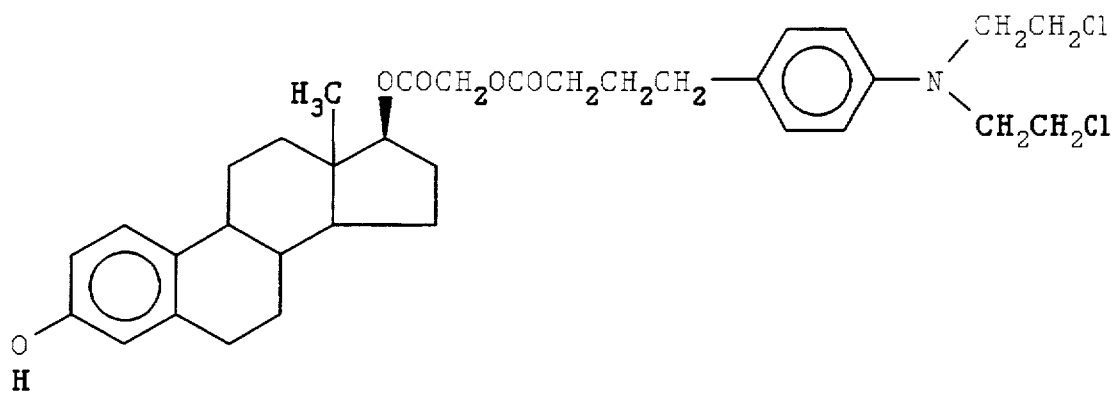

UNITED STATES PATENT AND TRADEMARK OFFICE
CERTIFICATE OF CORRECTION

PATENT NO. : 4,938,897
DATED : July 3, 1990
INVENTOR(S) : Kiro Asano et al.

It is certified that error appears in the above-indentified patent and that said Letters Patent is hereby corrected as shown below:

Columns 15 and 16, the structure which reads:

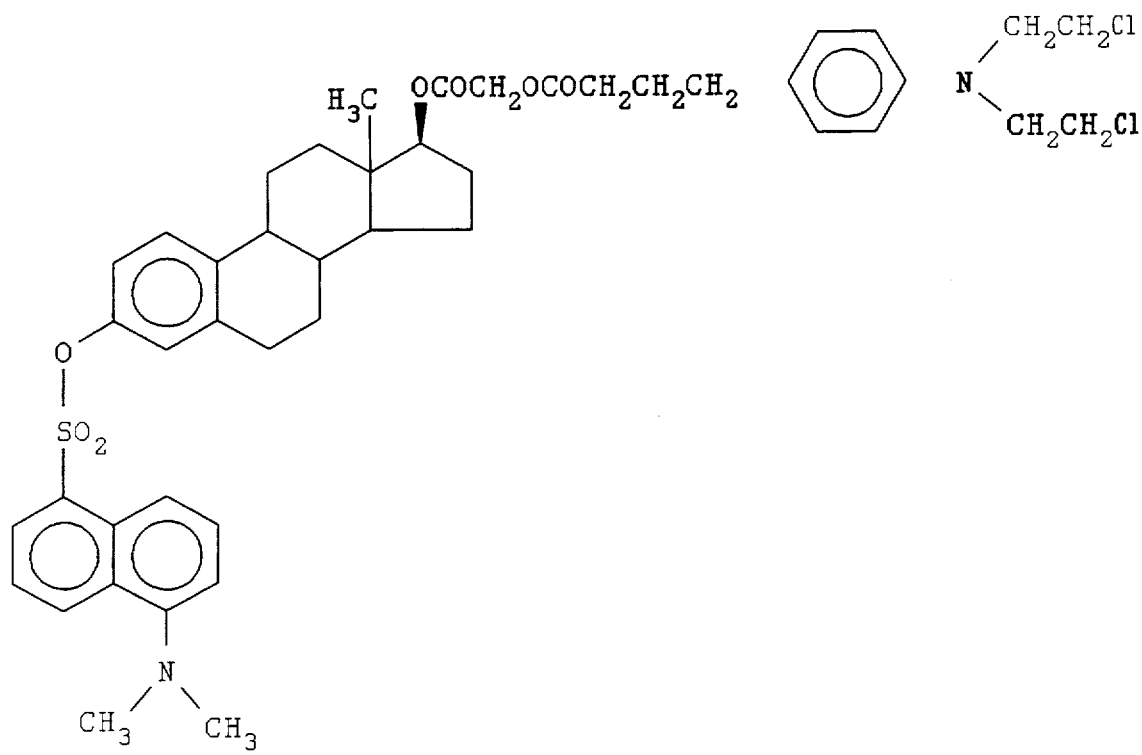

UNITED STATES PATENT AND TRADEMARK OFFICE
CERTIFICATE OF CORRECTION

PATENT NO. : 4,938,897
DATED : July 3, 1990
INVENTOR(S) : Kiro Asano et al.

Page 3 of 6

It is certified that error appears in the above-indentified patent and that said Letters Patent is hereby corrected as shown below:

should read:

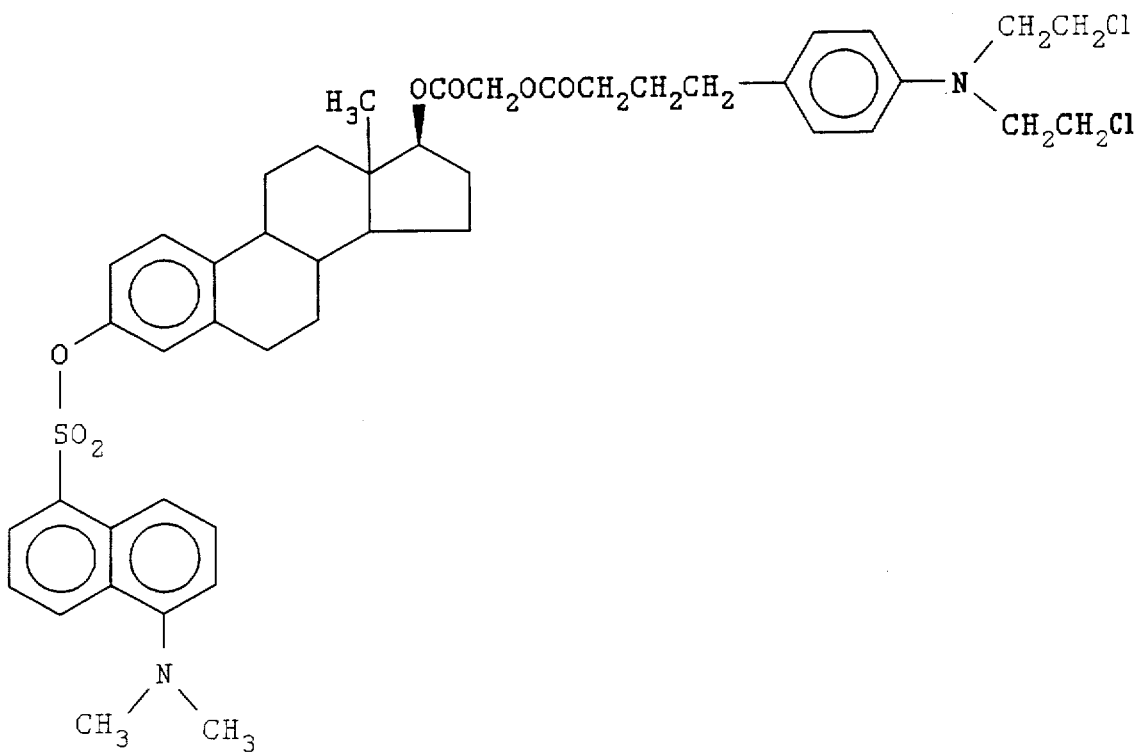

UNITED STATES PATENT AND TRADEMARK OFFICE
CERTIFICATE OF CORRECTION

PATENT NO. : 4,938,897
DATED : July 3, 1990
INVENTOR(S) : Kiro Asano et al.

Page 4 of 6

It is certified that error appears in the above-indentified patent and that said Letters Patent is hereby corrected as shown below:

Column 22, lines 1-9, the structure which reads:

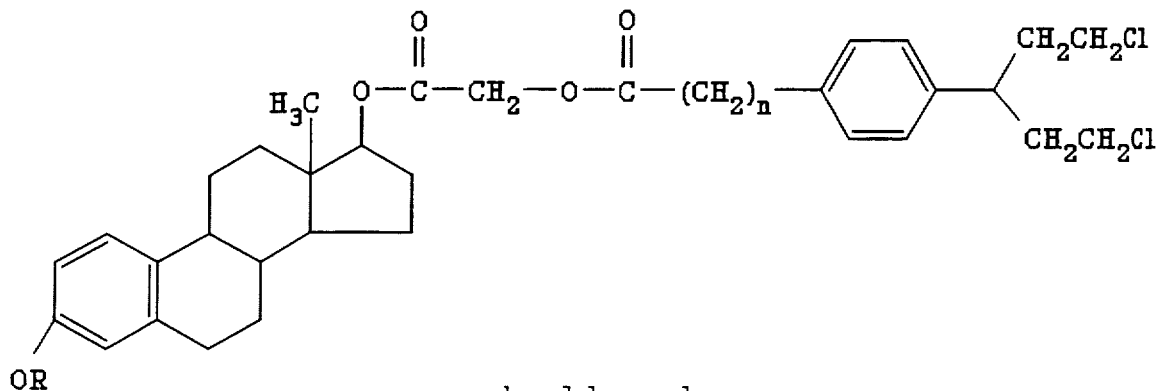

should read:

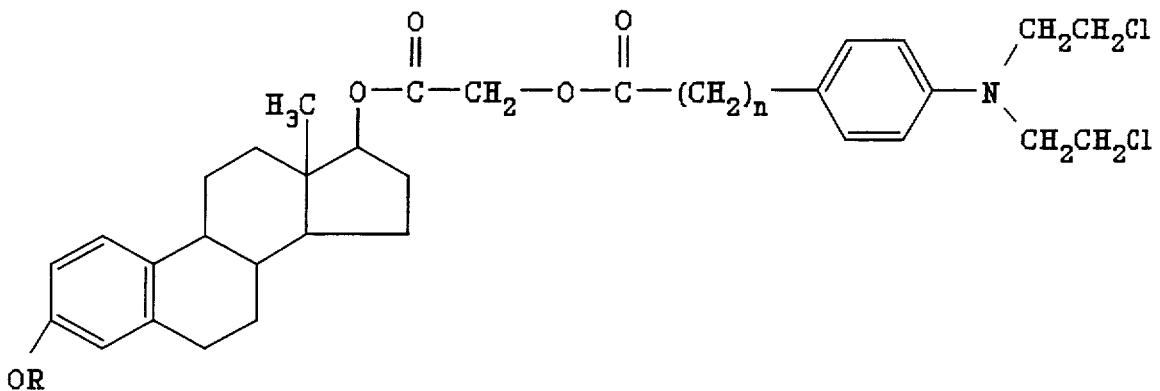

UNITED STATES PATENT AND TRADEMARK OFFICE
CERTIFICATE OF CORRECTION

PATENT NO. : 4,938,897

DATED : July 3, 1990

INVENTOR(S) : Kiro Asano et al.

It is certified that error appears in the above-indentified patent and that said Letters Patent is hereby corrected as shown below:

Column 22, lines 21-29, the structure which reads:

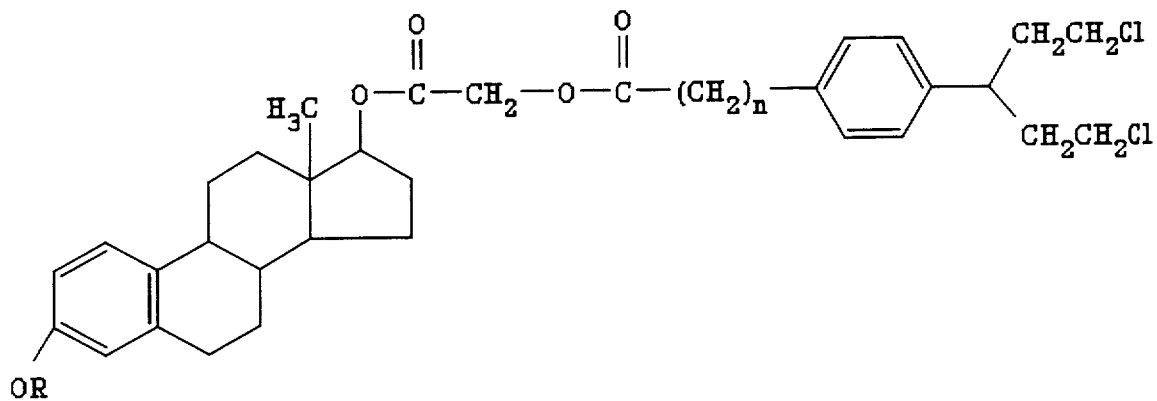

UNITED STATES PATENT AND TRADEMARK OFFICE
CERTIFICATE OF CORRECTION

PATENT NO. : 4,938,897
DATED : July 3, 1990
INVENTOR(S) : Kiro Asano et al.

It is certified that error appears in the above-indentified patent and that said Letters Patent is hereby corrected as shown below:

should read:

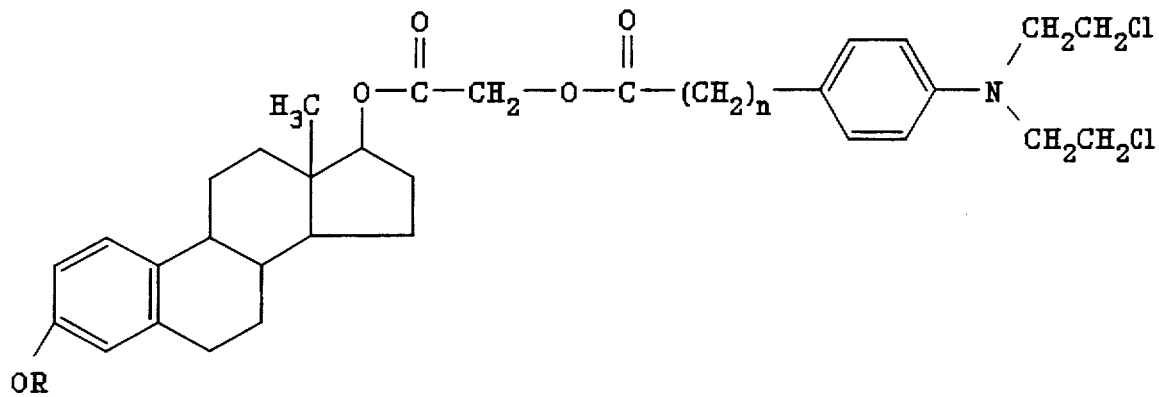

Signed and Sealed this

Twenty-sixth Day of December, 1995

Attest:

BRUCE LEHMAN

Attesting Officer

Commissioner of Patents and Trademarks